(12) United States Patent
Hoffman (10) Patent No.: US 7,778,382 B2
(45) Date of Patent: Aug. 17, 2010

(54) CT IMAGING SYSTEM WITH MULTIPLE PEAK X-RAY SOURCE

(75) Inventor: David M. Hoffman, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 64 days.

(21) Appl. No.: 11/465,472

(22) Filed: Aug. 18, 2006

(65) Prior Publication Data

US 2006/0285645 A1 Dec. 21, 2006

Related U.S. Application Data

(63) Continuation of application No. 10/250,132, filed on Jun. 5, 2003, now Pat. No. 7,120,222.

(51) Int. Cl.
*H05G 1/02* (2006.01)
*H01J 35/06* (2006.01)
*G21K 3/00* (2006.01)

(52) U.S. Cl. ............... 378/5; 378/16; 378/98.9; 378/134; 378/157; 378/158

(58) Field of Classification Search ............ 378/5, 378/9, 16, 19, 122, 124, 125, 134, 156, 157, 378/158, 159, 98.9, 98.11
See application file for complete search history.

(56) References Cited

U.S. PATENT DOCUMENTS

| | | | | |
|---|---|---|---|---|
| 3,610,984 A | * | 10/1971 | Seki et al. | 378/125 |
| 4,065,689 A | * | 12/1977 | Pleil | 378/134 |
| 4,445,226 A | * | 4/1984 | Brody | 378/98.9 |
| 4,686,695 A | * | 8/1987 | Macovski | 378/146 |
| 4,823,371 A | * | 4/1989 | Grady | 378/134 |
| 4,963,746 A | * | 10/1990 | Morgan et al. | 250/363.02 |
| 5,204,888 A | * | 4/1993 | Tamegai et al. | 378/53 |
| 5,485,492 A | * | 1/1996 | Pelc | 378/5 |
| 5,490,196 A | * | 2/1996 | Rudich et al. | 378/101 |
| 5,511,105 A | * | 4/1996 | Knott | 378/134 |
| 5,570,403 A | * | 10/1996 | Yamazaki et al. | 378/5 |
| 5,661,774 A | * | 8/1997 | Gordon et al. | 378/101 |
| 5,943,388 A | * | 8/1999 | Tumer | 378/98.9 |
| 6,036,362 A | * | 3/2000 | Schmitt | 378/206 |
| 6,104,781 A | * | 8/2000 | Buchmann | 378/101 |
| 6,188,747 B1 | * | 2/2001 | Geus et al. | 378/124 |
| 6,226,352 B1 | * | 5/2001 | Salb | 378/98.9 |
| 6,246,747 B1 | * | 6/2001 | Wear et al. | 378/98.9 |
| 6,307,918 B1 | * | 10/2001 | Toth et al. | 378/158 |
| 6,333,968 B1 | * | 12/2001 | Whitlock et al. | 378/136 |
| 6,449,333 B1 | * | 9/2002 | Yamasaki | 378/42 |
| 6,480,572 B2 | * | 11/2002 | Harris et al. | 378/136 |
| 6,553,096 B1 | * | 4/2003 | Zhou et al. | 378/122 |

(Continued)

*Primary Examiner*—Allen C. Ho (57) ABSTRACT

An x-ray source (32) for performing energy discrimination within an imaging system (10) includes a cathode-emitting device (82) for emitting electrons and an anode (81) that has a target (80) whereupon the electrons impinge to generate an x-ray beam (93) with multiple x-ray quantity energy peaks (116 and 120). A method of performing energy discrimination in the imaging system (10) includes emitting the electrons. The x-ray beam (93) with the x-ray quantity energy peaks (116 and 120) is generated. The x-ray beam (93) is directed through an object (44) and is thereafter received. An x-ray image having multiple energy differentiable characteristics is generated in response to the x-ray beam (93) as received.

20 Claims, 4 Drawing Sheets

U.S. PATENT DOCUMENTS

| | | | |
|---|---|---|---|
| 6,597,758 B1 * | 7/2003 | Rosner | 378/53 |
| 6,735,273 B2 * | 5/2004 | Flohr et al. | 378/5 |
| 6,760,407 B2 * | 7/2004 | Price et al. | 378/122 |
| 6,947,522 B2 * | 9/2005 | Wilson et al. | 378/125 |
| 6,968,030 B2 * | 11/2005 | Hoffman | 378/5 |
| 7,003,077 B2 * | 2/2006 | Jen et al. | 378/124 |
| 7,065,179 B2 * | 6/2006 | Block et al. | 378/134 |
| 7,187,756 B2 * | 3/2007 | Gohno et al. | 378/124 |
| 7,203,274 B2 * | 4/2007 | Charles, Jr. et al. | 378/54 |
| 2003/0195416 A1 * | 10/2003 | Toth | 600/427 |

* cited by examiner

CT IMAGING SYSTEM WITH MULTIPLE PEAK X-RAY SOURCE

RELATED APPLICATION

The present application is a continuation of U.S. patent application Ser. No. 10/250,132, which was filed on Jun. 5, 2003, entitled "CT Imaging System With Multiple Peak X-Ray Source," and issued as U.S. Pat. No. 7,120,222, and also is related to U.S. patent application Ser. No. 10/064,775, which was filed on Aug. 15, 2002, entitled "A Hybrid Scintillator/Photo Sensor & Direct Conversion Detector," and issued as U.S. Pat. No. 6,819,738, and which is incorporated herein by reference.

TECHNICAL FIELD

The present invention relates generally to multi-slice computed tomography (CT) imaging systems, and more particularly, to a system and method of performing energy discrimination therein.

BACKGROUND OF THE INVENTION

In computed topography (CT) imaging, portions of a patient are scanned and the density of materials contained therein are determined for various diagnostic and evaluation purposes. There is a continuous effort to increase CT imaging system scanning capabilities. Specifically, in CT imaging, it is desirable not only to be capable of determining density of scanned materials, but also to be able to distinguish between materials or combinations of materials that have similar densities.

For example, in certain testing procedures, in order to enhance visibility of blood and to better differentiate blood from other tissues or undesirable deposits within a vessel or organ, Iodide may be injected into the bloodstream of a patient. Combination of Iodide and water or blood, which consists mainly of water, and a combination of calcium deposits and soft tissue exhibit similar material densities, resulting in poor spatial and low contrast resolution between each combination and having effectively similar corresponding brightness levels when viewed by a practitioner. It is undesirable to have calcium build-up on inner linings of blood vessel walls. Thus, the practitioner, due to difficulty in discerning between the brightness levels of reconstructed CT images for the stated combinations, may not be able to determine whether there exists a calcium build-up in the blood vessels of the patient.

Figure 1:
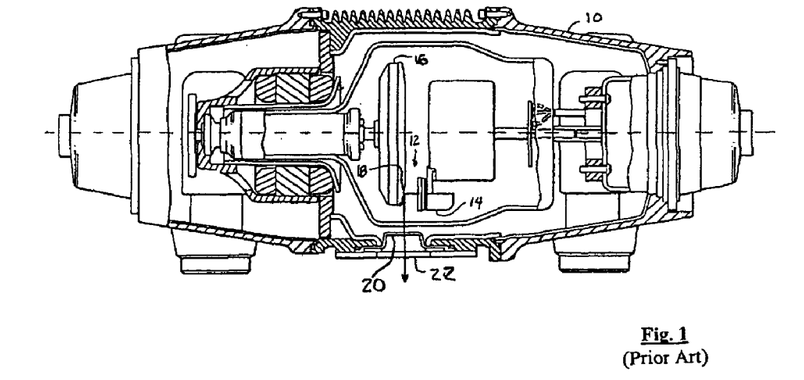
FIG. 1 is a cross-sectional view of a traditional CT tube assembly.

Referring now to FIG. 1, a cross-sectional view of a traditional CT tube assembly 10 is shown. CT imaging systems include a gantry that rotates at various speeds in order to create a 360° image. The gantry contains the CT tube assembly 10, which generates x-rays across a vacuum gap 12 between a single cathode 14 and an anode 16. In order to generate the x-rays, a large voltage potential is created across the vacuum gap 12 allowing electrons, in the form of an electron beam, to be emitted from the cathode 14 to a single target 18 of the anode 16. In releasing of the electrons, a filament contained within the cathode 14 is heated to incandescence by passing an electric current therein. The electrons are accelerated by the high voltage potential and impinge on the target 18, whereby they are abruptly slowed down to emit x-rays and form an x-ray beam that passes through a CT tube window 20.

Figure 2:
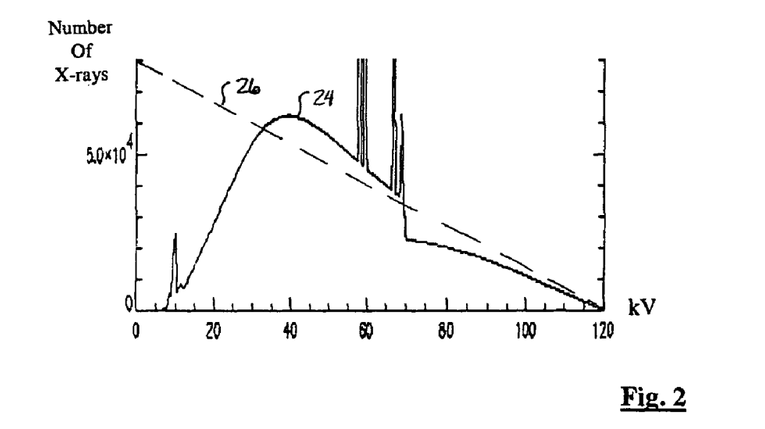
FIG. 2 is a pre-patient energy spectrum plot for the CT tube assembly of FIG. 1.

After passing through the CT tube window 20, the x-ray beam is filtered via a single filter 22. The filter 22 reduces the number of low energy x-rays that have energy levels below a predetermined energy level, thus reducing x-ray exposure to a patient. An example of a pre-patient energy spectrum plot of number of x-rays versus corresponding energy levels is shown in FIG. 2. A post-filter spectrum curve 24 overlays an approximate pre-filter spectrum curve 26. Notice that the spectrum curve 24 is single peaked and that the number of x-rays corresponding to energy levels below 40 KeV are significantly reduced, due to absorption by the filter 22.

The post filter x-rays pass through a portion of the patient and are detected by an x-ray detector array. As the x-rays pass through the patient, the x-rays become attenuated before impinging upon the detector array. X-ray attenuation measurements are generated by the x-ray detector corresponding to electrical signal response generated by the received x-rays having varying energy levels depending upon attenuation thereof. An x-ray image is reconstructed in response to the attenuation measurements.

The x-ray detector array generates an x-ray signal in response to the single peaked energy spectrum. Number of x-rays received by the detector is integrated over an average area of the detector and over a view time interval to generate an integrated signal. The integrated signal is directly related to densities of scanned materials of the patient. As is known in the art, it is difficult from the resulting energy spectrum and from inherent characteristics of integration to differentiate between similar material densities.

It would therefore be desirable to provide a CT system of energy discrimination to differentiate between different scanned materials and different scanned material combinations to increase CT scanning utility and capability. It would also be desirable for the CT system to be capable of performing energy discrimination with accuracy, clarity, and without increased x-ray exposure to a patient.

SUMMARY OF THE INVENTION

The present invention provides a system and method for performing energy discrimination within an imaging system. An x-ray source for performing energy discrimination within an imaging system is provided and includes a cathode-emitting device for emitting electrons and an anode that has a target whereupon the electrons impinge to generate an x-ray beam with multiple x-ray quantity energy peaks.

A method of performing energy discrimination in the imaging system is also provided, which includes emitting the electrons. The x-ray beam with the x-ray quantity energy peaks is generated. The x-ray beam is directed through an object and is thereafter received. An x-ray image having multiple energy differentiable characteristics is generated in response to the x-ray beam as received.

One of several advantages of the present invention is that it provides a system that is capable of performing energy discrimination, thus allowing a practitioner to differentiate between materials and material combinations having similar densities. In so doing, the present invention provides an increased yield of information for improved diagnostic, examination, testing, and evaluation purposes.

Another advantage of the present invention is that it provides improved spatial and low contrast resolution between different materials, thus further providing increased ease in differentiating between scanned materials.

Furthermore, the present invention provides energy discrimination while minimizing x-ray exposure to a patient.

The present invention itself, together with attendant advantages, will be best understood by reference to the following detailed description, when viewed in conjunction with the accompanying drawing figures.

BRIEF DESCRIPTION OF THE DRAWINGS

For a more complete understanding of this invention, reference should be made to the embodiments illustrated in detail in the accompanying drawing figures and also described below, by way of examples of the invention, wherein.

DETAILED DESCRIPTION OF THE PREFERRED EMBODIMENT

In each of the drawing figures discussed as follows, the same reference numerals are generally used to refer to the same or similar components. While the present invention is described with respect to a system and method for performing energy discrimination within a computed tomography (CT) imaging system, the following apparatus and method are capable of being adapted for various purposes and are not limited to the following applications: MRI systems, CT systems, radiotherapy systems, X-ray imaging systems, ultrasound systems, nuclear imaging systems, magnetic resonance spectroscopy systems, and other applications known in the art.

In the following description, various operating parameters and components are described for one constructed embodiment. These specific parameters and components are included as examples and are not meant to be limiting.

Also, in the following description, the term "x-ray quantity energy peaks" refers to the general shape of an energy spectrum plot and the peaks contained therein. An energy spectrum plot is a plot of x-ray energy levels and corresponding number of x-rays for each energy level. "X-ray quantity energy peaks," however, does not refer to mere sporadic spikes or minor or other insignificant data that may occur or exist within the energy plot. See FIG. 8 description below for a further detailed explanation.

Figure 3:
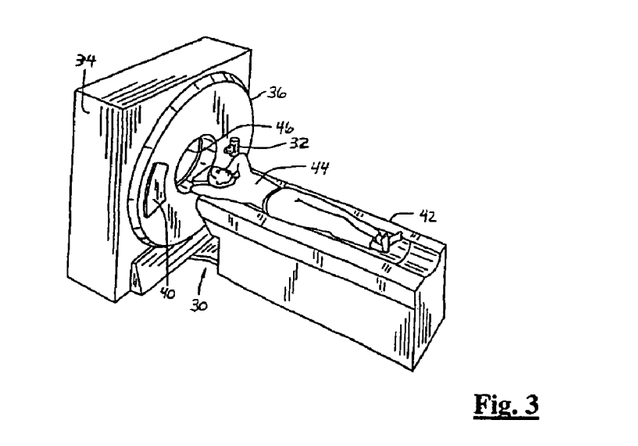
FIG. 3 is a perspective view of a CT imaging system including an x-ray source in accordance with an embodiment of the present invention.

Referring now to FIG. 3, a perspective view of a CT imaging system 30 including an x-ray source 32 in accordance with an embodiment of the present invention is shown. The imaging system 30 includes a gantry 34 that has a rotating inner portion 36 containing the x-ray source 32 and an energy-differentiating detector 40. The x-ray source 32 projects a beam of x-rays having multiple x-ray quantity energy peaks toward the detector 40. The source 32 and the detector 40 rotate about an operably translatable table 42. The table 42 is translated along a z-axis between the source 32 and the detector 40 to perform a helical scan. The beam, after passing through a medical patient 44 situated within a patient bore 46, is detected at the detector 40 so as to generate projection data that is used to create a CT image.

Figure 4:
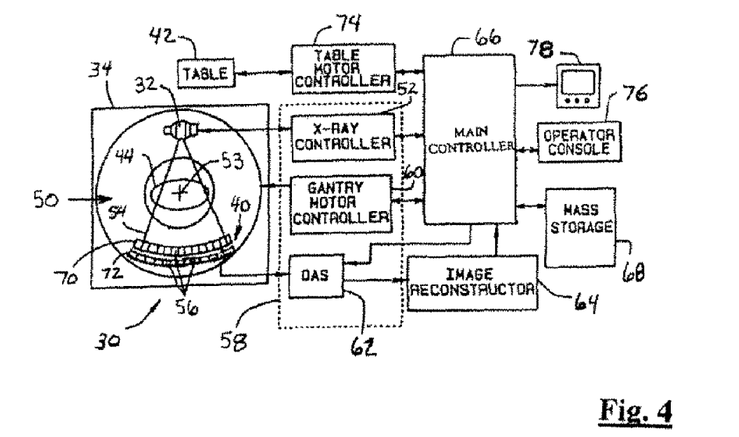
FIG. 4 is a cross-sectional close-up block diagrammatic view of a CT imaging system utilizing an energy discrimination system in accordance with an embodiment of the present invention.

Referring now to FIG. 4, a cross-sectional close-up block diagrammatic view of the imaging system 30 utilizing an energy discrimination system 50 in accordance with an embodiment of the present invention is shown. The energy discrimination system 50 includes the source 32, the detector 40, and an x-ray controller 52.

Generally, in operation the source 32 and the detector 40 rotate about a center axis 53. The beam 54 is received by multiple detector elements 56. Each detector element 56 generates an electrical signal corresponding to intensity of the impinging x-ray beam 54. As the beam 54 passes through the patient 44 the beam 54 is attenuated. Rotation of the inner portion 36 and operation of source 32 are governed by a control mechanism 58. Control mechanism 58 includes the x-ray controller 52 that provides power and timing signals to source 32 and a gantry motor controller 60 that controls the rotational speed and position of the inner portion 36. A data acquisition system (DAS) 62 samples analog data from the detector elements 56 and converts the analog data to digital signals for subsequent processing. An image reconstructor 64 receives sampled and digitized x-ray data from the DAS 62 and performs high-speed image reconstruction. A main controller 66 stores the CT image in a mass storage device 68.

The x-ray source 32 and the detector 40 rotate around an object to be imaged, such as the patient 44, so that the angle at which the beam intersects the object constantly changes. A group of x-ray attenuation measurements, i.e., projection data, from the detector 40 at one gantry angle is referred to as a "view." A "scan" of the object comprises a set of views made at different gantry angles during one revolution of the x-ray source 32 and the detector 40. In an axial scan, the projection data is processed so as to construct an image that corresponds to two-dimensional slices taken through the object.

One method for reconstructing an image from a set of projection data, projection data referring to a group of attenuation measurements, is referred to as the "filtered back-projection technique." This process converts the attenuation measurements from a scan into discrete integers, ranging from −1024 to +3072, called "CT numbers" or "Hounsfield Units" (HU). These HU's are used to control the brightness of a corresponding pixel on a cathode ray tube or a computer screen display in a manner responsive to the attenuation measurements. For example, an attenuation measurement for air may convert into an integer value of −1000 HU's (corresponding to a dark pixel) and an attenuation measurement for very dense bone matter may convert into an integer value of +3000 (corresponding to a bright pixel), whereas an attenuation measurement for water may convert into an integer value of 0 HU's (corresponding to a gray pixel). This integer conversion, or "scoring" allows a physician or a technician to determine the density of matter based on the intensity of the computer display and thus locate and identify areas of concern.

In one embodiment of the present invention, the detector 40 includes a first detector array 70 and a second detector array 72, as shown. The first array 70 may be a scintillator detector/ photo-sensor detector so as to allow for the collection of traditional information for creating anatomical detail for CT slices. The second array 72 may be a direct conversion (DC) detector, such as a cadmium zinc telluride detector, configured in an x-ray counting and energy discrimination mode to count attenuated x-rays and to measure attenuated x-ray energy.

Number and energy of the attenuated x-rays is used when performing energy discrimination to differentiate between material characteristics. Elemental composition and/or density of various tissue materials may be determined, such as differentiating between iodine, blood, calcium, or other materials known in the art. Information obtained from the arrays 70 and 72 may be super positioned to create a single image having identically positioned and overlapping information of anatomical detail and/or tissue discrimination (material type and density).

The second array 72 may be of a single slice design and/or a multiple slice design. The multiple slice design may provide information on a variety of different tissue materials, whereas the multiple slice design may be integrated across multiple slices for improved statistics on an individual basis. When the second array 72 is used in the x-ray counting and energy discrimination mode, x-ray dose added to the CT exam is minimized since a low quantity of x-rays are used to perform energy discrimination. To gather energy discrimination data a smaller amount of x-rays are used over a full or normal dose of x-rays, as used in a normal CT scan. A normal CT scan is performed with the first array 70 to provide detailed data, such as detailed anatomical data. When gathering energy discrimination data the second array 72 is used to generate an overlay image with material differentiating characteristics, such as tissue differentiating characteristic.

The above-described embodiment is for example purposes only. Although, it is preferred that at least one array be capable of detecting numbers of x-rays for various energy levels or ranges of energy levels, which are hereinafter referred to as x-ray quantity energy levels, any number of arrays may be used. For example, in the above-described embodiment array 72 is capable and configured to detect x-ray quantity energy levels, whereas array 70 is not. Also, each of the arrays 70 and 72 may be of various type and style and be in various configurations known in the art.

For a further detailed description of the detector 40 and various possible embodiments thereof, see patent application Ser. No. 10/064,775, which is entitled "A Hybrid Scintillator/Photo Sensor & Direct Conversion Detector," which issued as U.S. Pat. No. 6,819,738, and which is incorporated herein by reference.

The main controller 66 also receives commands and scanning parameters from an operator via an operator console 76. A display 78 allows the operator to observe the reconstructed image and other data from the main controller 66. The operator-supplied commands and parameters are used by the main controller 66 in operation of the x-ray controller 52, the gantry motor controller 60, and the DAS 62. In addition, the main controller 66 operates a table motor controller 74, which translates the table 42 so as to position the patient 44 in the gantry 34.

The x-ray controller 52, the gantry motor controller 60, the image reconstructor 64, the main controller 66, and the table motor controller 74 are preferably based on micro processors, such as a computer having a central processing unit, memory (RAM and/or ROM), and associated input and output buses. The x-ray controller 52, the gantry motor controller 60, the image reconstructor 64, the main controller 66, and the table motor controller 74 may be a portion of a central control unit or may each be stand-alone components as shown.

In the following embodiments a cathode-emitting device may refer to any electron emitting device or component. A cathode-emitting device may refer to a cathode, an x-ray tube kVp, a cathode-emitting surface, a cathode element, or other electron emitting device or component known in the art.

Figure 5:
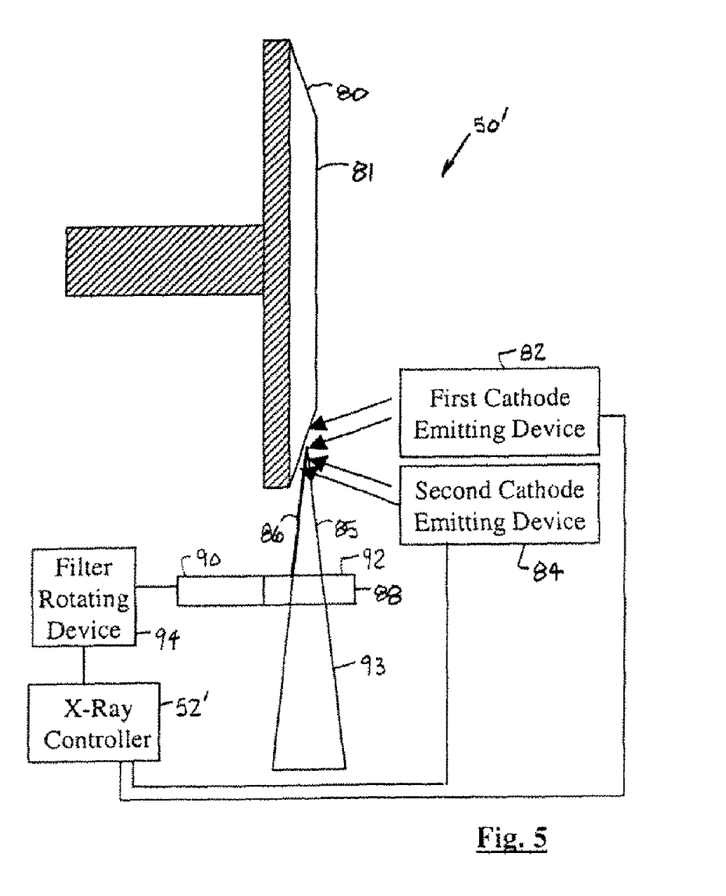
FIG. 5 is a cross-sectional close-up block diagrammatic view of an energy discrimination system having a single anode target in accordance with an embodiment of the present invention.

Referring now to FIG. 5, a cross-sectional close-up block diagrammatic view of an energy discrimination system 50'' having a single rotating target 80 of an anode 81, in accordance with an embodiment of the present invention, is shown. A first cathode-emitting device 82 and a second cathode-emitting device 84 emit electrons that are directed to impinge upon the target 80. A first kVp (kilovolt peak) exists between the first cathode-emitting device 82 and the anode target 80, which can be represented by a first approximately linear pre-filter spectrum curve of number of x-rays per energy level. A second kVp, that is different from that of the first kVp, exists between the second cathode-emitting device 84 and the anode target 80, which can be represented by a second approximately linear pre-filter spectrum curve of number of x-rays per energy level. The pre-filter spectrum curves may be represented using Cramer's Rule, as is known in the art. The first kVp pre-filter spectrum curve is different in slope than that of the second kVp pre-filter spectrum curve.

Upon impact with the target 80, x-rays in the form of x-ray beams 85 and 86 are generated and directed through a rotating filter 88. The rotating filter 88 includes a first filter 90 and a second filter 92, and each of the filters 90 and 92 has different energy-absorbing characteristics. Although, a rotating filter is utilized, some other filtering device having two or more filters may be used. In one embodiment, each filter 90 and 92 prevents passage of x-rays corresponding to energy levels below associated predetermined energy levels for each of the x-ray beams 85 and 86. In effect, the filters 90 and 92, for the stated embodiment, are acting as high-pass filters. Of course, the filters may each perform as a band pass, notch, low pass, digital, or other type of filter as known in the art.

The x-ray beams 85 and 86 are mixed upon passing through the filters 90 and 92 to generate a mixed or composite post-filter beam 93 having multiple x-ray quantity energy peaks, due to generation of different quantities of electrons at associated energy levels therein by the devices 82 and 84 and different absorbing characteristics of the filters 90 and 92. The filters 90 and 92, in effect, may have different energy pass ranges so as to allow x-rays within a predetermined energy range to pass through the filters 90 and 92. The energy pass ranges may be of any size and be associated with any energy level or levels.

An x-ray controller 52', is electrically coupled to the devices 82 and 84 and to a filter rotating device 94, which is coupled to and rotates the filter 88. The controller 52', synchronously transitions between the devices 82 and 84 and the filters 90 and 92, respectively. The controller 52' may be in the form of or an integral part of the x-ray controller 52 or the main controller 66, may be a separate controller, or may be some other controller known in the art.

Figure 6:
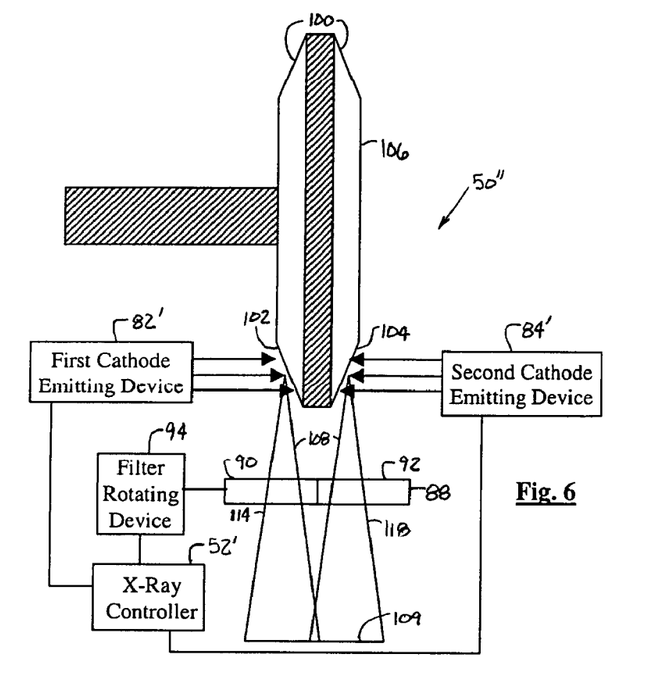
FIG. 6 is a cross-sectional close-up block diagrammatic view of an energy discrimination system having dual anode targets in accordance with another embodiment of the present invention.
Figure 8:
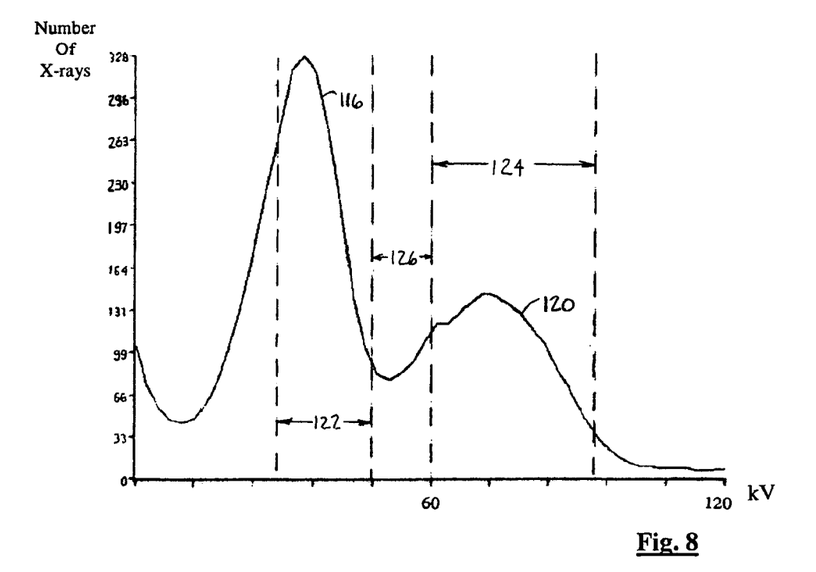
FIG. 8 is a pre-patient energy spectrum plot for an x-ray source in accordance with another embodiment of the present invention.

Referring now to FIG. 6, a cross-sectional close-up block diagrammatic view of an energy discrimination system 50'' having dual anode rotating targets 100, in accordance with another embodiment of the present invention, is shown. A first cathode-emitting device 82' and a second cathode-emitting device 84' emit electrons that are directed to impinge upon a first rotating target 102 and a second rotating target 104 of an anode 106, respectively. A first kVp exists between the first cathode-emitting device 82' and the rotating target 102, and a second kVp exists between the second cathode-emitting device 84' and the rotating target 104, in a fashion similar to that of the embodiment in FIG. 5. Upon impact with the targets 102 and 104, x-rays in the form of x-ray beams 108 are generated and directed through the rotating filter 88, whereupon exiting the filter 88 they are mixed to generate a mixed or composite post-filter beam 109. Although the rotating filter 88 is utilized, some other filtering device having one or more filters may be used. The filters 90 and 92 may be transitional or may be stationary. The beam 109 has two or more x-ray quantity energy peaks, as is best shown in FIG. 8.

As with the embodiment of FIG. 5, the controller 52' is electrically coupled to the emitting devices 82' and 84' and to the filter rotating device 94, which is coupled to and rotates the filter 88. The controller 52', synchronously transitions between the devices 82' and 84' and the filters 90 and 92, respectively. In an alternative embodiment, the filters 90 and 92 are stationary and the devices 82' and 84' are operated simultaneously.

FIGS. 5 and 6 illustrate two possible embodiments of the present invention, other embodiments may be easily envisioned by one skilled in the art. There may exist any number of anode targets, cathode-emitting devices, and filters. For example, the first cathode-emitting device 82 and the second cathode-emitting device 84 may be replaced by a single cathode-emitting device operating so as to generate and transition between two different kVps. Also, more than two cathode-emitting devices and/or filters may be used to generate a beam having any number of x-ray quantity energy peaks. These examples are described in further detail below.

Although, it is preferred for accuracy, resolution, and clarity purposes to have at least two cathode-emitting devices and at least two filters, as is shown in the embodiments of FIGS. 5 and 6, various quantities of each may be used.

In a couple alternative embodiments of the present invention, the embodiments of FIGS. 5 and 6 are modified such that only a single cathode-emitting device is used in combination with the rotating filter 88. The first filter 90 and the second filter 92 are alternated therebetween for a single x-ray beam to generate a post-patient x-ray beam having a dual peaked energy spectrum. The single cathode-emitting device may have a quickly varying kVp, which may be used in conjunction with a transitioning or rotating filter.

In a further pair of alternative embodiments of the present invention, the embodiments of FIGS. 5 and 6 are modified, such that the cathode-emitting devices 82, 82', 84, and 84' are utilized in conjunction with a single stationary filter instead of the rotating filter 88. The cathode-emitting devices 82 and 84 and the cathode-emitting devices 82' and 84' are alternated, respectively, therebetween to generate x-ray beams having different energy spectrum profiles or distributions of the number of x-rays per energy level.

Figure 7:
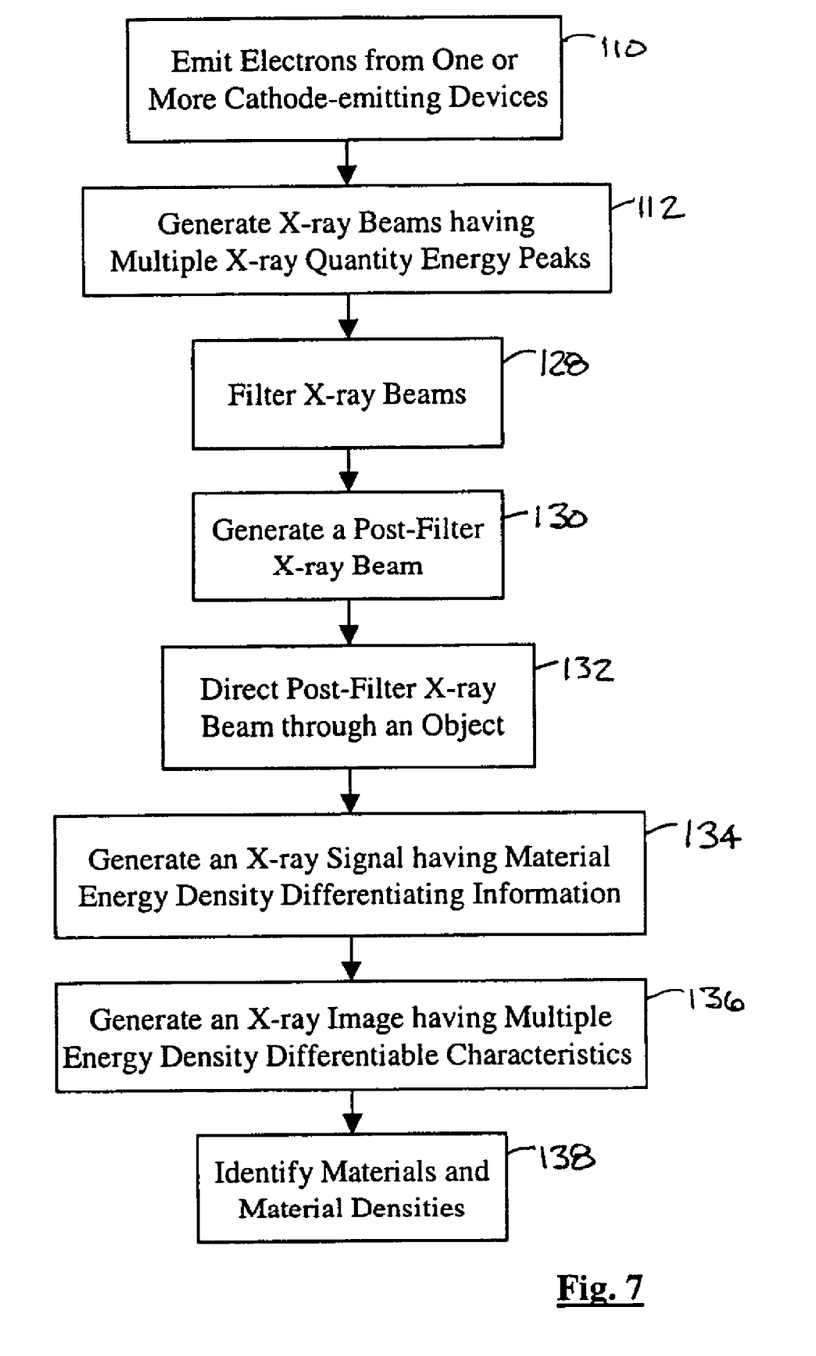
FIG. 7 is a logic flow diagram illustrating a method of performing energy discrimination in an imaging system in accordance with an embodiment of the present invention.

Referring now to FIG. 7, a logic flow diagram illustrating a method of performing energy discrimination in an imaging system in accordance with an embodiment of the present invention is shown. For simplicity, the method of FIG. 7 is described with respect to the embodiments of FIGS. 5 and 6, but is not limited to the stated embodiments.

In step 110, one or more cathode-emitting devices, such as emitting devices 82, 82', 84, and 84', emit electrons to impinge upon one or more anode targets, such as targets 80, 102, and 104, as described above.

In step 112, x-ray beams, such as beams 86 and 108, are generated having multiple x-ray quantity energy peaks. For example, a first x-ray beam 114 having a first x-ray quantity energy peak 116 and a second x-ray beam 118 having a second x-ray quantity energy peak 120 may be generated; beams 114 and 118 are best seen in FIG. 6 and peaks 116 and 120 are best seen in the pre-patient energy spectrum plot of FIG. 8. The first x-ray quantity energy peak 116 and the second x-ray quantity energy peak 120 are generated by respective kVp of each cathode-emitting device 82' and 84' and filtering of each x-ray beam 108 by the filters 90 and 92.

Although, in this described embodiment the energy spectrum plot has only a pair of peaks 116 and 120, an energy spectrum plot may have any number of peaks, by altering the number of cathode-emitting devices, filters, and correlations between the cathode-emitting devices and the filters. The peaks 116 and 120 may correspond to predetermined energy bins 122 and 124, as shown, which may be separated by one or more separation zones 126 (only one is shown) having significantly reduced quantities of x-rays. The bins 122 and 124 and the separation zones 126 aid in accurately differentiating between materials having similar material energy densities.

Referring again to FIG. 7, in step 128, the x-ray beams are filtered, via the rotating filter 88. The controller 52' transitions between the first filter 90 and the second filter 92. The controller 52' transitions between the filters 90 and 92 at least once for each view in a scan of the patient 44.

In step 130, the x-ray beams are mixed so as to generate a mixed or composite post-filter x-ray beam, such as beam 93 or beam 109 in FIGS. 5 and 6, having multiple x-ray quantity energy peaks.

In step 132, the post-filter x-ray beam is directed through at least a portion of the patient 44.

In step 134, the detector 40 receives the post-filter x-ray beam and in response thereto generates an x-ray signal having material energy density differentiating information, such as numbers of x-rays per energy level, contained therein. The x-ray detector 40 may measure x-ray quantity energy levels of the x-ray beams corresponding to each of the peaks 116 and 120 and may measure x-ray quantity energy levels corresponding to the energy bins 122 and 124 to aid in simplifying energy discrimination of multiple materials having similar energy densities. The detector 40 or other signal conditioning devices known in the art may signal condition the x-ray signal such that separations between x-ray quantity energy peaks are effectively magnified, by filtering out undesired predetermined energy density levels.

In step 136, the system 30 generates an x-ray image having multiple energy density differentiable characteristics, such as image contrast levels, brightness levels, color variations, or other differentiating characteristic known in the art, in response to the x-ray signals.

In step 138, materials and material densities of the scanned portion of the patient 44 are identified. The materials and material densities may be determined by a practitioner, by the main controller 66, or by some other device or technique known in the art. In having multiple x-ray energy peaks, materials or material combinations having similar densities may be easily differentiated, since each material or material combination exhibits different x-ray energy peak profiles.

The x-ray energy peak profiles may be further used to generate different image material differentiating characteristics. For example, a first material combination may exhibit a dual peaked energy spectrum having a first magnitude set of values for each peak and a second material combination may also exhibit a dual peaked energy spectrum, but having a second and different magnitude set of values for each peak. The differences in magnitude or peak values between the two material combinations may be illustrated in an x-ray image through use of one or more of the above-mentioned differentiating characteristics.

The above-described steps are meant to be an illustrative example; the steps may be performed synchronously, sequentially, simultaneously, or in a different order depending upon the application.

The present invention provides an energy discrimination system and method for easily differentiating between materials and material combinations that have similar energy densities. The present invention provides this increased performance capability and improved spatial and low contrast resolution while minimizing x-ray exposure to a patient.

The above-described apparatus, to one skilled in the art, is capable of being adapted for various purposes and is not limited to control systems or other communication systems. The above-described invention may also be varied without deviating from the spirit and scope of the invention as contemplated by the following claims.

What is claimed is:

1. A method of scanning a patient, said method comprising the steps of
   (a) establishing a first electron-accelerating voltage potential between a first cathode and an anode;
   (b) establishing a second electron-accelerating voltage potential between a second cathode and said anode;
   (c) emitting a first plurality of electrons from said first cathode and toward said anode so that said first plurality of electrons impinge on said anode and thereby generate a first x-ray beam;
   (d) emitting a second plurality of electrons from said second cathode and toward said anode so that said second plurality of electrons impinge on said anode and thereby generate a second x-ray beam;
   (e) directing first x-ray beam and said second x-ray beam in alternating pulses through a filter device so as to form an alternating pulse composite x-ray beam;
   (f) directing said alternating pulse composite x-ray beam through said patient and thereafter receiving said alternating pulse composite x-ray beam with a detector so as to accordingly generate x-ray signals; and
   (g) generating an x-ray image in response to said x-ray signals;
   wherein said first electron-accelerating voltage potential has a characteristic first kilovolt peak, said second electron-accelerating voltage potential has a characteristic second kilovolt peak, and said second kilovolt peak is different from said first kilovolt peak.

2. A method as set forth in claim 1, wherein said anode includes a single rotating target upon which said first plurality of electrons and said second plurality of electrons impinge.

3. A method as set forth in claim 2, wherein steps (c) and (d) are performed in an alternating manner.

4. A method as set forth in claim 1, wherein said anode includes a first rotating target upon which said first plurality of electrons impinge, and said anode includes a second rotating target upon which said second plurality of electrons impinge.

5. A method as set forth in claim 4, wherein steps (c) and (d) are performed in an alternating manner.

6. A method as set forth in claim 1, wherein said filter device includes a first filter and a second filter that respectively have different energy-absorbing characteristics.

7. A method as set forth in claim 1, wherein said alternating pulse composite x-ray beam is formed so as to have a plurality of x-ray quantity-versus-energy peaks.

8. A method as set forth in claim 1, wherein said detector includes at least one array of multiple detector elements for generating said x-ray signals according to the energy intensity of said composite x-ray beam.

9. A method as set forth in claim 1, wherein said x-ray image is generated so as to have differentiable energy-density characteristics on a display.

10. A method of scanning a patient, said method comprising the steps of:
    (a) establishing a first electron-accelerating voltage potential between a first cathode and an anode;
    (b) establishing a second electron-accelerating voltage potential between a second cathode and said anode;
    (c) emitting a first plurality of electrons from said first cathode and toward said anode so that said first plurality of electrons impinge on said anode and thereby generate a first x-ray beam;
    (d) emitting a second plurality of electrons from said second cathode and toward said anode so that said second plurality of electrons impinge on said anode and thereby generate a second x-ray beam;
    (e) directing said first x-ray beam and said second x-ray beam through a filter device so as to form a composite x-ray beam;
    (f) directing said composite x-ray beam through said patient and thereafter receiving said composite x-ray beam with a detector so as to accordingly generate x-ray signals; and
    (g) generating an x-ray image in response to said x-ray signals;
    wherein said first electron-accelerating voltage potential has a characteristic first kilovolt peak, said second electron-accelerating voltage potential has a characteristic second kilovolt peak, and said second kilovolt peak is different from said first kilovolt peak;
    wherein said anode includes a first rotating target upon which said first plurality of electrons impinge, and said anode includes a second rotating target upon which said second plurality of electrons impinge; and
    wherein steps (c) and (d) are performed simultaneously.

11. A method of scanning a patient, said method comprising the steps of:
    (a) establishing a first electron-accelerating voltage potential between a first cathode and an anode;
    (b) establishing a second electron-accelerating voltage potential between a second cathode and said anode;
    (c) emitting a first plurality of electrons from said first cathode and toward said anode so that said first plurality of electrons impinge on said anode and thereby generate a first x-ray beam;
    (d) emitting a second plurality of electrons from said second cathode and toward said anode so that said second plurality of electrons impinge on said anode and thereby generate a second x-ray beam;
    (e) directing said first x-ray beam and said second x-ray beam in an alternating fashion through a filter device so as to form an alternating pulse composite x-ray beam having a plurality of x-ray quantity-versus-energy peaks;
    (f) directing said alternating pulse composite x-ray beam through said patient and thereafter receiving said alternating pulse composite x-ray beam with an energy-differentiating detector so as to accordingly generate x-ray signals according to the energy intensity of said alternating pulse composite x-ray beam; and
    (g) generating an x-ray image in response to said x-ray signals so that said x-ray image has differentiable energy-density characteristics on a display;
    wherein said first electron-accelerating voltage potential has a characteristic first kilovolt peak, said second electron-accelerating voltage potential has a characteristic second kilovolt peak, and said second kilovolt peak is different from said first kilovolt peak.

12. A method as set forth in claim 11, wherein said anode includes a single rotating target upon which said first plurality of electrons and said second plurality of electrons impinge, and steps (c) and (d) are performed in an alternating manner.

13. A method of scanning a patient, said method comprising the steps of:
(a) establishing a first electron-accelerating voltage potential between a first cathode and an anode;
(b) establishing a second electron-accelerating voltage potential between a second cathode and said anode;
(c) emitting a first plurality of electrons from said first cathode and toward said anode so that said first plurality of electrons impinge on said anode and thereby generate a first x-ray beam;
(d) emitting a second plurality of electrons from said second cathode and toward said anode so that said second plurality of electrons impinge on said anode and thereby generate a second x-ray beam;
(e) directing said first x-ray beam and said second x-ray beam through a filter device so as to form a composite x-ray beam having a plurality of x-ray quantity-versus-energy peaks;
(f) directing said composite x-ray beam through said patient and thereafter receiving said composite x-ray beam with an energy-differentiating detector so as to accordingly generate x-ray signals according to the energy intensity of said composite x-ray beam; and
(g) generating an x-ray image in response to said x-ray signals so that said x-ray image has differentiable energy-density characteristics on a display;
wherein said first electron-accelerating voltage potential has a characteristic first kilovolt peak, said second electron-accelerating voltage potential has a characteristic second kilovolt peak, and said second kilovolt peak is different from said first kilovolt peak;
wherein said anode includes a first rotating target upon which said first plurality of electrons impinge, said anode includes a second rotating target upon which said second plurality of electrons impinge, and steps (c) and (d) are performed simultaneously.

14. A method of scanning a patient, said method comprising the steps of:
emitting a first plurality of electrons from a first cathode and toward an anode so that said first plurality of electrons impinge on said anode and thereby generate a first x-ray beam;
emitting a second plurality of electrons from a second cathode and toward said anode so that said second plurality of electrons impinge on said anode and thereby generate a second x-ray beam;
directing said first x-ray beam and said second x-ray beam alternately through a filter device so as to form an x-ray beam with alternating characteristics;
directing said alternating characteristic x-ray beam through said patient and thereafter receiving said alternating characteristic x-ray beam with a detector so as to accordingly generate x-ray signals; and
generating an x-ray image in response to said x-ray signals;
wherein said filter device includes a first filter and a second filter that respectively have different energy-absorbing characteristics; and
wherein said filter device is operable to rotatably interchange the respective positions of said first filter and said second filter as said first x-ray beam and said second x-ray beam are respectively directed through said filter device.

15. A method of scanning a patient, said method comprising the steps of:
emitting a first plurality of electrons from a first cathode and toward an anode so that said first plurality of electrons impinge on said anode and thereby generate a first x-ray beam;
emitting a second plurality of electrons from a second cathode and toward said anode so that said second plurality of electrons impinge on said anode and thereby generate a second x-ray beam;
directing said first x-ray beam and said second x-ray beam in an alternating fashion through a filter device so as to form a alternating pulse composite x-ray beam having a plurality of x-ray quantity-versus-energy peaks;
directing said alternating pulse composite x-ray beam through said patient and thereafter receiving said alternating pulse composite x-ray beam with an energy-differentiating detector so as to accordingly generate x-ray signals according to the energy intensity of said alternating pulse composite x-ray beam; and
generating an x-ray image in response to said x-ray signals so that said x-ray image has differentiable energy-density characteristics on a display;
wherein said filter device includes a first filter and a second filter that respectively have different energy-absorbing characteristics, and said filter device is operable to rotatably interchange the respective positions of said first filter and said second filter as said first x-ray beam and said second x-ray beam are respectively directed through said filter device.

16. A system for scanning a patient, said system comprising:
a first cathode operable to emit a first plurality of electrons;
a second cathode operable to emit a second plurality of electrons;
an anode for thereon impinging said first plurality of electrons and said second plurality of electrons in an alternating fashion so as to respectively generate a first x-ray beam alternating with a second x-ray beam;
a filter device operable to filter said first x-ray beam and said second x-ray beam so as to form an alternating pulse composite x-ray beam;
a detector operable to receive said composite x-ray beam after being directed through said patient and accordingly generate x-ray signals;
a display operable to generate an x-ray image in response to said x-ray signals; and
at least one controller electrically coupled to said first cathode, said second cathode, said anode, said filter device, said detector, and said display;
wherein said filter device includes a first filter and a second filter that respectively have different energy-absorbing characteristics; and
wherein said controller is operable to control said filter device so as to rotatably interchange the respective positions of said first filter and said second filter as said first x-ray beam and said second x-ray beam are respectively directed through said filter device.

17. A system as set forth in claim 16, wherein said anode is rotatable.

18. A system as set forth in claim 16, wherein said anode includes a single rotatable target upon which said first plurality of electrons and said second plurality of electrons can impinge.

19. A system as set forth in claim 16, wherein said anode includes a first rotatable target upon which said first plurality of electrons can impinge, and said anode includes a second rotatable target upon which said second plurality of electrons can impinge.

20. A system as set forth in claim 16, wherein said detector includes at least one array of multiple detector elements for generating said x-ray signals according to the energy intensity of said composite x-ray beam.

* * * * *